United States Patent [19]

Dombek

[11] Patent Number: 4,703,064

[45] Date of Patent: Oct. 27, 1987

[54] PROCESS FOR PRODUCING ALCOHOLS

[75] Inventor: Bernard D. Dombek, Charleston, W. Va.

[73] Assignee: Union Carbide Corporation, Danbury, Conn.

[21] Appl. No.: 555,637

[22] Filed: Nov. 28, 1983

Related U.S. Application Data

[63] Continuation-in-part of Ser. No. 279,095, Jun. 30, 1981, abandoned, and a continuation-in-part of Ser. No. 359,778, Mar. 19, 1982, abandoned, which is a continuation of Ser. No. 91,242, Nov. 11, 1979, abandoned.

[51] Int. Cl.⁴ .................. C07C 27/06; C07C 67/00
[52] U.S. Cl. ................................ 518/700; 560/232; 560/263; 560/265
[58] Field of Search ............... 518/700; 560/232, 263, 560/265

[56] References Cited

U.S. PATENT DOCUMENTS 3,833,634 9/1974 Pruett et al. .
3,855,307 12/1974 Rony et al. .
4,301,253 11/1981 Warren .
4,315,993 2/1982 Knifton .

FOREIGN PATENT DOCUMENTS 2024811 1/1980 United Kingdom ................ 518/700

OTHER PUBLICATIONS

Fonseca et al., High Pressure Science & Technology, Sixth AIRAPT Conference, Plenum Press, N.Y. 1979, pp. 733–738.
Keim et al., J. of Catalysis, 61, 359–365 (1980).
Bradley, J.A.C.S., 10124 (1979), pp. 7419–7421.

Primary Examiner—Howard T. Mars
Attorney, Agent, or Firm—S. T. Trinker

[57] ABSTRACT

This invention relates to the manufacture of valuable alcohols containing 1 to 2 carbon atoms, especially ethylene glycol, methanol, and ethanol, from the reaction of hydrogen and carbon monoxide, by a homogeneous catalytic process using as the catalyst a synergistic mixture of solubilized ruthenium carbonyl complexes.

31 Claims, 8 Drawing Figures

PROCESS FOR PRODUCING ALCOHOLS

This is a continuation-in-part of patent application Ser. No. 279,095, filed June 30, 1981, and a continuation-in-part of patent application Ser. No. 359,778, filed Mar. 19, 1982, which in turn is a continuation of patent application Ser. No. 91,242, filed Nov. 11, 1979, all now abandoned each of said applications are incorporated herein by reference.

This invention relates to an improved process, and the catalyst which achieves this process, for making ethylene glycol, methanol, and ethanol directly from synthesis gas, i.e., mixtures of hydrogen and carbon monoxide. More particularly, this invention achieves the production of ethylene glycol directly from synthesis gas using a particular synergistic combination of ruthenium carbonyl complexes under process conditions. This invention encompasses a process of producing ethylene glycol, methanol, and ethanol directly from the reaction of synthesis gas in the presence of a stable ruthenium catalyst. The process of this invention is distinctive in the stability of the process, avoiding any significant loss of ruthenium values from reaction and in the catalyst employed.

DISCUSSION OF THE PRIOR ART

Owing to the limited availability of petroleum sources the cost of producing chemicals from petroleum has been steadily increasing. Many have raised the dire prediction of significant oil shortages in the future. Obviously, a different low cost source is needed which can be converted into the valuable chemicals now derived from petroleum sources. Synthesis gas is one such source which can be effectively utilized in certain circumstances to make chemicals.

The most desirable aspect of synthesis gas is that it can be produced from non-petroleum sources. Synthesis gas is derived by the combustion of any carbonaceous material including coal, or any organic material, such as hydrocarbons, carbohydrates and the like. Synthesis gas has for a long time been considered a desirable starting material for the manufacture of a variety of chemicals. A number of chemicals have been made commercially from synthesis gas. Hydrocarbons have been made by the Fischer-Tropsch catalytic reaction. Methanol is commercially manufactured by a heterogeneous catalytic reaction from synthesis gas. Aldehydes and alcohols are made from the reaction of olefins and synthesis gas. If one could expand the production of chemicals in a commercial manner from synthesis gas then one would not be as presently dependent upon petroleum as the basic raw material even though it is an excellent raw material for making synthesis gas. Accordingly, intense interest in such processes has developed.

Pruett and Walker, U.S. Pat. No. 3,833,634, patented Sept. 3, 1974, based on an application originally filed Dec. 21, 1971, describe a process for preparing glycols by reacting an oxide of carbon with hydrogen using a rhodium carbonyl complex catalyst. The examples of the patent compare the reaction of hydrogen and carbon monoxide in the presence of the desired rhodium containing catalyst and other metals. In Example 9 of the patent, the reaction was attempted with triruthenium dodecacarbonyl as the catalyst using tetrahydrofuran as the solvent with a reaction temperature of 230° C., for 2 hours, and "the product contained no polyhydric alcohol." As will be shown below, Pruett and Walker apparently failed to produce polyhydric alcohols because they did not run at the conditions of reaction long enough and/or with enough ruthenium containing catalyst to achieve reaction to produce at least a detectable amount of a polyhydric alcohol such as ethylene glycol. Unquestionably, ruthenium is not as active a catalyst source to produce glycol as is rhodium under the conditions investigated.

Gresham, U.S. Pat. No. 2,535,060, describes a process for preparing monohydric alcohols by introducing carbon monoxide, hydrogen and a hydroxylated solvent into a reaction vessel and heating the mixture in the presence of a ruthenium-containing substance and an alkaline reagent which controls the pH within the range of 7 to 11.5, at a temperature within the range of 150° to 300° C. under a pressure within the range of 200 to 1,000 atmospheres.

Solid ruthenium dioxide is used in Examples 1 and 2 of the aforementioned Gresham patent. At column 2, lines 30-33 of the patent, the patentee states his belief that ruthenium dioxide is reduced in situ during the reaction. Example 1 compares the use of a number of solutes such as phosphoric acid, acidic phosphate buffer, no solutes at all, ammonia and sodium bicarbonate. In this example the solvent was water. In Example 2 of Gresham, a number of alcohols were characterized as solvents.

Gresham states that ruthenium and its compounds are "specific" in their effect upon this reaction and other catalysts "do not lead to straight chain primary alcohols under the conditions of this process". There is no indication that Gresham's process, as operated by him, produced ethylene glycol.

Gresham's work should be contrasted with his earlier work described in U.S. Pat. No. 2,636,046, filed Oct. 16, 1948. In this patent, Gresham describes the production of polyfunctional oxygen-containing organic products including such compounds as ethylene glycol, glycerine, and the like.* This is accomplished by the reaction of hydrogen with carbon monoxide in the presence of a solvent to produce glycol. According to this patent, the reaction of carbon monoxide with hydrogen must be at pressures of above 1,000 atmospheres and "particularly above a minimum of about 1,400 atmospheres" in order to obtain the "polyfunctional oxygen-containing organic compounds . . . in excellent yield" (column 2, lines 9–17). The patent specifically states at column 2, lines 37-43, that:

"[I]n the hydrogenation of oxides of carbon at pressures of 1,000 atmospheres and below, virtually no polyfunctional compounds are produced At pressures above 1,000 atmospheres and especially at pressures of about 1,500 to 5,000 atmospheres, preferably 2,000 to 5,000 atmospheres, polyfunctional compounds are obtained."

Though the examples of the patent describe only the use of cobalt catalyst, the patentee, at column 3, line 61, indicates that the catalyst may contain "cobalt, ruthenium, etc." According to the patentee, the most outstanding results are obtained by using a catalyst containing cobalt, especially compounds of cobalt which are soluble in at least one of the ingredients of the reaction mixtures.

* Note the evaluation of this work by Rathke and Feder, J. Am. Chem. Soc., 100, pp. 3623-3625 (May 24, 1978).

According to Roy L. Pruett, Annals, New York Academy of Sciences, Vol. 295, pages 239-248 (1977), at page 245, metals other than rhodium were tested to determine the production of ethylene glycol from mixtures of carbon monoxide and hydrogen. These metals include cobalt, ruthenium, copper, manganese, iridium and platinum. Of these metals, only cobalt was found to have a slight activity, citing British Pat. No. 665,698 which corresponds generally to the last mentioned Gresham U.S. Patent. Pruett stated that such slight activity with cobalt was "qualitatively" in agreement with the results obtained by Ziesecke, 1952, Brennstoff-Chem, 33:385.

Prior to the filing of U.S. Patent No. 2,535,060 and subsequent to the filing of U.S. Pat. No. 2,636,046, there was filed on Apr. 12, 1949, a commonly assigned application by Howk, et al. which issued as U.S. Pat. No. 2,549,470 on Apr. 17, 1951. The Howk, et al. patent is directed to a catalytic process for making monohydric straight chain alcohols and does not mention the production of ethylene glycol. The patent emphasizes the production of straight chain primary hydroxyalkanes having from 3 to 50 or more carbon atoms in the molecule. This, the patent states, is accomplished by introducing hydrogen, carbon monoxide, and a hydroxylated solvent into a reaction vessel, and heating the mixture in the presence of a catalyst of the class consisting of ruthenium metal, ruthenium oxide and ruthenium carbonyl, at a pressure within the range of 200 to 1,000 atmospheres and at a temperature within the range of 100° to 250° C. The liquid hydroxyl-containing reaction medium may be water or alcohol, preferably a primary hydroxyalkane having from 1–10 carbon atoms per molecule. According to the patentee, a substantial proportion of the reaction product usually consists of alcohols containing more than 6 carbon atoms per molecule. The patent goes on to state (column 1, line 50, et seq.):

"The reaction products usually contain virtually no hydrocarbons, acids, esters, or branched-chain alcohols. These results were entirely unexpected, in view of the existing knowledge of the catalytic reaction between carbon monoxide and hydrogen in the presence of alchols and Group VIII metal catalysts."

According to the Howk, et al. patent:

"It should be emphasized here that, under the conditions of temperature, pressure and gas ratios just described, no reaction takes place between carbon monoxide and hydrogen in a liquid medium (water or alcohol) if one of the common group VIII metals, such as cobalt or nickel, is used as the catalyst. This is evidenced by the fact that, using, for example, a cobalt catalyst, no significant drop in pressure is observed when carbon monoxide and hydrogen are contacted under the conditions recited. Ruthenium is thus unexpectedly different from these related metals." (Column 4, lines 19–30.)

The numbered examples indicate an apparent preference for making normal-monohydric alcohols, with the proportion of pentane soluble to pentane insoluble alcohol being at least 2:1. In one example, starting at the bottom of column 6 of Howk, et al., the solvent employed is characterized as a carboxylic acid or anhydride rather than the neutral hydroxylated solvents which were described in the other examples. This comparative example demonstrated that in a process operated at 200° C. for 18 hours using pressures maintained in the range of 300–950 atmospheres by repressurizing periodically with synthesis gas, there was produced a reaction product containing "a large quantity of wax." According to the author, 40.55 parts of esters boiling from 59° C. at atmospheric pressure to 150° C. at 116 millimeters pressure were obtained and this can be compared to the wax obtained in the amount of 37.06 parts. In that particular example, the patentee appears to have demonstrated that when the hydroxylated solvent is not employed, the amount of wax essentially equals the amount of pentane soluble alcohol products obtained. This is supported by the statement at column 2 of Gresham U.S. Pat. No. 2,535,060 which refers to Howk, et al.

At column 3, lines 54 et seq., Howk, et al. describe the influence that pressure has on the course of the reaction. According to Howk, et al. with pressures up to about 150 atmospheres the reaction products are only hydrocarbons. This appears to be in accord with recent work described by Masters, et al. in German Patent Application (Offenlegungsschrift), No. 2,644,185*, based upon British priority application Specification No. 40,322-75, filed Oct. 2, 1975. Masters, et al. obtained only hydrocarbons at such pressures using a ruthenium catalyst.

* See Doyle, et al., *J. of Organometallic Chem.*, 174, C55-C58 (1979), who conclude that the process characerized in the German Offenlegungsschrift involved a heterogeneous Fischer-Tropsch reaction.

Fenton, U.S. Pat. No. 3,579,566, patented May 18, 1971, is concerned with a process of reducing organic acid anhydrides with hydrogen in the presence of a Group VIII noble metal catalyst and a biphyllic ligand of phosphorus, arsenic or antimony. The process of Fenton bears a remarkable similarity to oxo processing conditions to produce aldehydes and alcohols (compare with Oliver, et al., U.S. Pat. No. 3,539,634, patented November 10, 1970) except that Fenton fails to supply an olefinic compound to the reaction. In the reaction of Fenton, an acid anhydride, such as acetic acid anhydride, is reduced to ethylidene diacetate in the presence of hydrogen and a rhodium halide or a mixture of palladium chloride and ruthenium trichloride catalyst, provided in combination with triphenylphosphine. Ethylene glycol diacetate is. also observed. Carbon monoxide, which is added to some of the examples of Fenton, is described by Fenton, at column 2, lines 48–51, as follows: "If desired, a suitable inert gas, such as carbon monoxide can also be charged to the reaction zone . . . ". (Emphasis added). Of particular significance is the fact that none of Fenton's examples produce a methyl ester. Another point is that Fenton's ethylidene diacetate can be thermally cracked to produce vinyl acetate, see column 1, lines 42–44. It would seem possible that such occurred in Example 1 of Fenton and it is further possible that acetic acid added to the vinyl acetate to form ethylene glycol diacetate.

In European Patent Application No. 13,008, published July 7, 1980, there is, among other things, described a process for producing methyl and ethylene glycol esters by reacting carbon monoxide and hydrogen in a homogenous liquid phase mixture comprising a ruthenium carbonyl complex and acyl compound such as acetic acid. The reaction is effected at a temperature between about 50° C. to about 400° C. and a pressure of between about 500 psia (35.15 kg/cm$^2$) and about 12,500 psia (878.84 kg/cm$^2$) for a period of time sufficient to produce such esters as the predominant product.

In copending application Ser. No. 205,025, filed Nov. 4, 1980, there is described an improved process for producing methyl and ethylene glycol esters as described in the European Patent Application in which the combined concentration of methyl ester, ethylene glycol ester and water in the reaction medium is maintained at less than about 30 vol. %.

In the European Patent Application there is also described an improved process for making the products methanol, ethylene glycol, and ethanol or mixtures thereof, at relatively low pressures.

An interesting exception to the previously reported inactivity of ruthenium catalysts to produce glycol is the high pressure (viz 1650–1750 bars) experiment reported by Fonseca, Jenner, Kiennemann, and Deluzarche, et al., High Pressure Science and Technology, 6th AIRAPT Conference (Chapt. "High Pressure Synthesis of Polyalcohols by Catalytic Hydrogenation of Carbon Monoxide"), pages 733–738 (1979), published by Plenum Press, New York (see also a discussion of the same work in Erdol und Kohle, 32, 313 (1979)). The authors report the reaction in tetraglyme of a $CO:H_2$ (1:2 ratio) mixture at 1650–1765 bars, i.e., about 25,000 psi (1,757.6 $Kg/cm^2$) and 230° C. using triruthenium dodecacarbonyl and 2-pyridinol as a ligand, both in unstated amounts, for a period of 5 hours. The authors report a percent conversion of 12.9 (unstated basis), and percent yield of polyols of 3 (unstated basis), and percent selectivities as follows: ethylene glycol, 22.9; glycerine, 0; methanol, 16.1. However, in a manuscript entitled "Reactions $CO-H_2$ in Liquid Phase in Presence of Ruthenium Catalysts," by Jenner, Kiennemann, Bagherzadah, and Deluzarche, (React. Kim. Catal. Letters, 15, 103 (1980).) it is stated that with respect to the above experiment "We never could reproduce the run with $Ru_3(CO)_{12}$ when operating in a vessel which has not been in contact with any rhodium catalyst We suspect that in the former run, the formation of ethylene glycol was due to catalysis with metallic sediments of rhodium encrusted on the wall of the vessel (we showed that ethylene glycol is produced in appreciable yield with rhodium foam)".* In Williamson, et al., U.S. Pat. No. 4,170,605 patented Oct. 9, 1979 the patentees report in Examples I and II the reaction in 1-propanol of synthesis gas ($CO:H_2=1:1$) at 25,000 psig and at 230° C. using ruthenium tris(acetylacetonate) and 2-hydroxypyridine, the latter being the same ligand employed by Fonseca, et al, supra, for a period of 2 and 3 hours, respectively. In Example 1, Williamson, et al., report the production of 4 grams of product containing (mole percent basis): ethylene glycol, 57; and methanol 25. In Example II, 7 grams of product are reported containing 66 and 16 mole percent of ethylene glycol and methanol, respectively.

* This report may be relevant to the reports by Williamson et al, (infra) and Keim et al, (infra).
** Included in the 4 and 7 grams of product are trace amounts of water and methylformate as well as 16 mole percent (Example I) and 15 mole percent (Example II) of propylformate. The latter compound would appear to be derived from 1-propanol initially present in the reaction mixture, rather than a synthesis gas-derived product.

W. Keim, et al., (Journal of Catalysis, 61, 359 (1980)) has reported that reactions of $Ru_3(CO)_{12}$ under very high pressures (2,000 bars) produce mainly methanol and methyl formate, but traces of glycol (0.8 to 1.2 percent of the total products) were also seen. In one experiment a small amount of ethanol was detected. No glycerine was observed in these reactions.

In a recent report (J. Am. Chem. Soc., 101, 7419 (1979).), J. S. Bradley of Exxon Corporation reported the production of methanol and methyl formate at a selectivity greater than 99% without hydrocarbon products detected, by the reaction of synthesis gas ($H_2:CO=3:2$) under pressures on the order of 1,300 atmospheres and at temperatures around 270° C. using a Ru catalyst. Bradley observed that no ethanol, ethylene glycol, or acetates formed. Compare this result with that found by Pruett and Walker, supra, and the work of Fonseca, et al. and Williamson, et al., infra.

As pointed out above, ethylene glycol can be produced directly from a mixture of hydrogen and carbon monoxide using a rhodium carbonyl complex as a catalyst. The literature describes (see U.S. Pat. No. 3,957,857, issued May 18, 1976) that a desirable rhodium compound can be in the form of a rhodium carbonyl cluster compound, particularly one which exhibits a particular 3-band infrared spectral pattern. There has been a substantial amount of work done on the formation of ethylene glycol from mixtures of hydrogen and carbon monoxide in the presence of rhodium carbonyl clusters, such as is described in U.S. Pat. Nos. 3,833,634; 3,878,214; 3,878,290; 3,878,292; etc. to name but a few.

For the purposes of the discussion and descriptions contained herein, mixtures of hydrogen and carbon monoxide, regardless of the amount of each present, will be characterized, for the sake of convenience, as "synthesis gas". Thus, mole ratios of hydrogen to carbon monoxide of e.g. 40 to 1 and 0.05 to 1 are arbitrarily classified as "synthesis gas". Where the molar ratio of one or the other is significant to the invention herein described, then specific reference to the desired molar ratio will be made.

SUMMARY OF THE INVENTION

Figure 1:
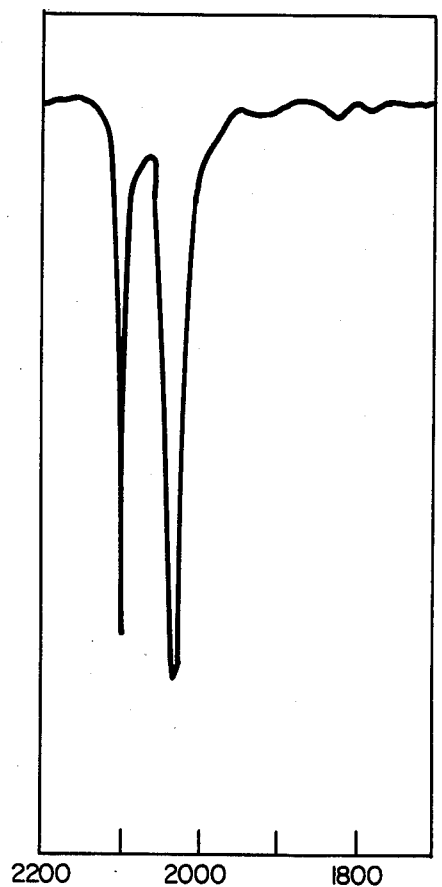
FIG. 1 depicts the infrared spectrum of PPN [$Ru(CO)_3I_3$], (PPN designates bis[triphenylphosphine]iminium), prior to use in the process.

The process of this invention relates to the production of ethylene glycol in a homogeneous liquid phase reaction by employing a synergistic mixture of a ruthenium carbonyl iodide-containing complex and a ruthenium carbonyl hydrido complex. The ruthenium catalyst employed in the process is indicated by the presence of two ruthenium carbonyl complexes, i.e., $Ru(CO)_3I_3^-$ and $HRu_3(CO)_{11}^-$, which constitute a synergistic combination indicating the ruthenium catalyst which is characterized by an infrared spectrum characterized by three significant infrared bands between about plus or minus 10 $cm^{-1}$ of about 2100 $cm^{-1}$, 2015 $cm^{-1}$, and 1990 $cm^{-1}$.

The process of this invention involves the conversion of synthesis gas, however derived, into a limited variety of valuable alcohol compounds which themselves can be directly consumed or which can be employed as starting materials to make other valuable chemicals. The process of this invention is concerned with making 2 carbon atom alcohols, to wit, ethanol and ethylene glycol and in particular, ethylene glycol. In addition, the process of this invention also produces methanol. The process of this invention is capable of producing predominantly ethylene glycol or predominatly methanol, or predominantly ethanol, or mixtures of them each in large concentrations. The process of this invention provides the capability of a low cost route to methanol, ethanol and ethylene glycol, especially ethylene glycol.

One of the deficiencies of certain of the aforementioned processes for making ethylene glycol from synthesis gas was the utilization of a rhodium carbonyl complex as the catalyst, which processes are dependent on the high price of rhodium. The high cost of rhodium is created by its limited availability and the tremendous demand for it. (For example rhodium presently is employed in catalytic converters which comprise the automotive combustion devices for reducing automotive pollutant emissions.) Thus, a commercial process which uses rhodium as a catalyst is affected by the high capital expense to purchase the metal and the stringent controls needed to limit catalyst losses in order to keep the economics of the process competitive.* Ruthenium, on the other hand, is a precious metal which presently has no significant commercial application. Its present cost is approximately 1/20th, and less, that of rhodium even though its concentration in the ore from which both are obtained is about the same. Ruthenium has been explored as a catalyst by many, as is shown by the discussed references, supra. It has been considered as a hydrogenation catalyst, as a hydroformylation catalyst, as a catalyst to produce a wide range of monohydric alcohols (non-specific as to any of them) exclusive of methanol, as an alcohol homologation catalyst such as for the conversion of methanol to ethanol,** as a high pressure catalyst to selectively produce methanol and methyl formate, and its inactivity as a catalyst to produce glycol has been noted above.

* See Cornils, et al., Hydrocarbon Processing, June, 1975, pp. 83 to 91.
** See, for example, U.S. Pat. Nos. 4,133,966 and 3,285,948; and Japanese Patent Application (Kokai) No. 52-73804/77 (June 21, 1977) [Application No. 50-149391/75 (application date, Dec. 15, 1975)] to Mitsubishi Gas Chemical Industry Company.

DETAILED DESCRIPTION OF THE INVENTION

This process constitutes a relatively low pressure process for selectively converting synthesis gas to such valuable chemicals as ethylene glycol, ethanol and methanol. Also produced by the process of this invention are glycerol (i.e. glycerine), 1,2-propylene glycol, 1-propanol and methyl formate. However, the process of this invention is mainly concerned with the production of ethylene glycol (the most valued product) and to a lesser extent ethanol and methanol, since they are produced in significantly greater amounts than the other products. The process of this invention is accomplished by the presence of a synergistic combination of two ruthenium carbonyl complexes.

The process of this invention is carried out with a synergistic mixture of ruthenium carbonyl complexes present in a solvent, even though such complexes may exist during the reaction in more than one liquid phase. In this sense, the reaction is termed a homogeneous liquid phase reaction. There may be more than one such phase existing in the reaction zone but the ruthenium catalyst, as indicated by the presence of the two ruthenium carbonyl complexes, is always dissolved in at least one of such phases and is always in a dissolved liquid state. The problem with employing heterogeneous ruthenium catalysis in the reaction zone is that such will induce the Fischer-Tropsch reaction resulting in the formation of hydrocarbons and/or a variety of oxygenated hydrocarbons having a variety of molecular weights with low selectivity to any one compound. In fact, the presence of such products suggests that undissolved ruthenium is present and that a non-homogeneous liquid phase reaction occurred.

The process of this invention involves the solubilization of ruthenium and the presence of the synergistic combination of ruthenium carbonyl complexes in the presence of synthesis gas at temperatures, pressures and for a period of time sufficient to produce ethylene glycol. Such conditions are set forth herein. In simplistic and in the broadest terms, the invention comprises the solubilization under the reaction conditions (i.e., time, temperature and pressure) of a ruthenium source, preferably ruthenium in the absence of any other platinum group metals (viz., platinum, palladium, rhodium and iridium),* in an appropriate solvent under a prescribed synthesis gas pressure to provide a ruthenium carbonyl catalyst characterized by the synergistic mixture of ruthenium carbonyl complexes $Ru(CO)_3I_3^-$ and $HRu(CO)_{11}^-$ which mixture is characterized by an infrared spectrum having three significant infrared bands between about plus or minus $10 \text{ cm}^{-1}$ of about $2100 \text{ cm}^{-1}$, $2015 \text{ cm}^{-1}$, and $1990 \text{ cm}^{-1}$. Further, other infrared bands are usually observed at $2070 \text{ cm}^{-1}$, $1955 \text{ cm}^{-1}$ and $1720 \text{ cm}^{-1}$ (see FIGS. 1–4). It will be appreciated that the exact position of said infrared bands may be dependent on the solvent employed, counter-ions present, the presence of ligands and the like, but in most cases will be within $\pm 10 \text{ cm}^{-1}$ of the above stated value. The reaction conditions comprise (i) a period of time at a temperature and pressure which cause the hydrogen and carbon monoxide to react to produce the desired products (ii) a temperature between about 50° C. and 400° C. and (iii) a pressure between 500 psia (35.15 kg/cm$^2$) and 15,000 psia (1,054.6 kg/cm$^2$). The catalyst of this invention is indicated by the presence of three significant infrared bands, and

* See U.S. Pat. No. 3,989,799, patented Nov. 2, 1976, wherein ruthenium is a cation in a mixed metal rhodium-containing carbonyl complex.

The process of this invention is distinctive in the selection of materials which comprise the homogeneous liquid phase mixture, the reaction parameters and the stability of the ruthenium containing catalyst in most cases, indeed, in all cases studied. As with any technology, this process has undergone evolutionary changes and its further examination will undoubtedly bring more changes, most likely in the form of additional or substitutional steps and/or materials.

It is known that this process may be carried out in the presence of a promoter although selection of the promoter is not clearly understood. A promoter, in the context of this invention, is a material provided to the reaction which provides a promotional effect in that it enhances the production (viz., rate, yield, or efficiency) of any of the products, or it improves the selectivity of the reaction toward ethylene glycol rather than methanol or ethanol, or it improves the selectivity of the reaction to ethanol rather than methanol irrespective of the amount of ethylene glycol produced, or it helps to reduce the loss of ruthenium during the reaction. Typical of the promoters that are believed capable of being employed in the instant process are Lewis base promoters (such as those described in European Patent Application No. 13,008, incorporated by reference herein) to the extent that such promoter enhances the instant process.

The solvent is selected such that the solvent is capable of maintaining the ruthenium carbonyl complex catalyst in the homogeneous liquid phase mixture throughout the reaction. The solvent may possibly provide an additional benefit such as influencing the kinds of ion pairing that exist during the course of the reaction.

The catalyst of this invention is a ruthenium carbonyl catalyst which contains carbon monoxide directly bonded to ruthenium (ruthenium carbonyl). The ruthenium compound which is provided to the reaction is not necessarily in a form which will effectively catalyze the reaction even if it contains a carbon monoxide ligand bonded to it. Ruthenium compounds such a ruthenium salts, oxides and carbonyl clusters may be introduced to the reaction in a condition which allows them to be solubilized, and under the conditions of the reaction they are converted into carbonyl complexes which effectively catalyze the reaction. The composition and structure of the ruthenium carbonyl complexes which catalyze the desired reaction are not specifically known but their presence is indicated by a mixture of two ruthenium carbonyl complexes, i.e. $Ru(CO)_3I_3^-$ and $HRu_3(CO)_{11}^-$, having a characteristic infrared spectrum characterized by three significant infrared bands between about plus or minus 10 $cm^{-1}$ of about 2100 $cm^{-1}$, 2015 $cm^{-1}$, and 1900 $cm^{-1}$. Varied reaction conditions, solvents, ligands, counter-ions, and promoters (if employed), may result in different amounts of the desired products of the process, and different rates, efficiencies and/or yields, but it is believed that although each provides a different and distinct catalytic evironment that the synergistic mixture of ruthenium carbonyls aforementioned and the characteristic infrared spectrum will be present.

The aforementioned ruthenium carbonyl catalyst of this invention is also characterized by having an average oxidation state of between about $-0.2$ and about 0.25. The average oxidation state of the synergistic combination of the ruthenium carbonyl complexes is calculated by taking the oxidation state of a ruthenium atom in $HRu_3(CO)_{11}^-$ as $-\frac{1}{3}$ and the oxidation state of a ruthenium atom in $Ru(CO)_3I_3^-$ as $+2$. Accordingly, the average oxidation state of a 2:1 molar ratio of $HRu_3(CO)_{11}^-$ to $Ru(CO)_3I_3^-$ is zero and such average oxidation state is most preferred. Similarly, as above discussed, ruthenium-containing compounds which provide the ruthenium carbonyl catalyst of this invention may be employed.

The ruthenium-containing substances which may be employed in the practice of this invention to form the catalyst, as characterized by the synergistic ruthenium carbonyl mixture, under process conditions encompass those which are described, for example, in Gresham, U.S. Pat. No. 2,535,060 at column 2, starting at line 38 to line 48, and ruthenium carbonyl compounds. It generally is not advisable to place ruthenium compounds or substances on a support material for use in the process of this invention because such offers no benefits over solubilizing such ruthenium compounds in combination with the aforementioned solvent and/or promoter. Moreover, ruthenium deposited on a support material can be expected to be solubilized in the homogeneous liquid phase reaction system of this invention as it is contacted with carbon monoxide. Ruthenium oxides, such as dioxide, sesquioxide, or tetraoxide, may be converted to the ruthenium carbonyl complex employed in the process of this invention. Ruthenium carbonyl compounds (which include ruthenium carbonyl hydrides or ruthenium carbonyl clusters) are already provided with a carbonyl ligand, and under the conditions of the reaction can be sufficiently changed to achieve the desired catalytic effect. Ruthenium salts such as those of organic acids can be employed in the practice of this invention to produce the catalyst. In addition to those ruthenium compounds described in the aforementioned Gresham patent, one may employ ruthenium compounds of bidentate ligands, allyl complexes, arene complexes, halides, and alkyl complexes. The choice of ruthenium compounds is varied and not critical to this invention so long as the aforementioned characteristic infrared spectrum is observed. A number of ruthenium complexes are known to be more stable to the presence of carbon monoxide than other ruthenium compounds and the skilled worker can determine which particular ruthenium compound might take longer to initiate a reaction than other ruthenium compounds. On that basis, one can select for the purposes of convenience the particular ruthenium compound to be utilized in forming the catalyst. However, ruthenium which is associated with an organic molecule or complexed with carbon monoxide is most readily solubilized so as to provide a readily available source of the ruthenium carbonyl catalyst of this process.

Although the exact nature of the actual ruthenium catalyst is not precisely known, the presence of an active catalytic system is indicated by the presence (either before, during or after the process is carried out) of a synergistic mixture of $Ru(CO)_3I_3^-$ and $HRu_3(CO)_{11}^-$. This mixture can be initially provided to the process or formed in situ, such as by the reaction of $Ru_3(CO)_{12}$ with excess $I^-$ as follows:

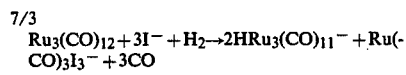

Selection of the ruthenium-containing starting material is important if in situ formation is desired since it has been observed that use of Ru(II) or Ru(III) halide complexes which do not form the synergistic mixture of $Ru(CO)_3I_3^-$ and $HRu_3(CO)_{11}^-$ do not provide the ruthenium catalyst employed in the process of this invention. However, such Ru(II) or Ru(III) complexes may be converted to the ruthenium catalyst according to this invention by reaction with appropriate base and an iodide containing compound. For example, if the ruthenium compound is $RuI_3$ the following depicts the conversion of such compound:

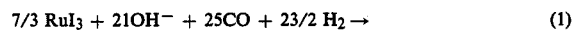

(1)

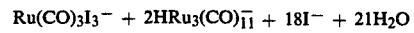

The complex $Ru(CO)_3I_3^-$ may be converted to an active Ru catalyst as follows:

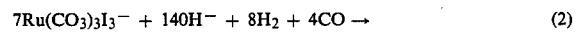

(2)

-continued $$Ru(CO)_3I_3^- + 2HRu_3(CO)_{11}^- + 18I^- + 14H_2O$$

Similarly, the Ru catalyst according to the invention maybe prepared by employing $HRu_3(CO)_{11}^-$ as follows:

$$7/3 HRu_3(CO)_{11}^- + 7/6 I_2 + \tfrac{8}{3} I^- \rightarrow \qquad (3)$$
$$Ru(CO)_3I_3^- + 2HRu_3(CO)_{11}^- + \tfrac{8}{3} CO + 1/6\, H_2$$

In addition, the presence of the ruthenium complex catalyst of this invention is indicated by a reaction mixture having an infrared spectrum characterized by three significant infrared bands between about plus or minus 10 cm$^{-1}$ of about 2100 cm$^{-1}$, 2015 cm$^{-1}$ and 1990 cm$^{-1}$.

As characterized by equations (1), (2) and (3) the formation of the catalyst according to this invention is inhibited by the addition of base (reducing agent) and acid (oxidizing agent) beyond that required to give the ruthenium catalyst.

As characterized above, this process is operated as a homogeneous liquid phase mixture. The process is typically carried out in a solvent for the catalyst. The solvent is a liquid in which the catalyst components are soluble under the prescribed conditions of the reaction. The solvent may be solid at room temperature but should at least, in part, be a liquid under the conditions of reaction.

A preferred solvent is a liquid at reaction conditions which is polar or complexes ions. Of the polar solvents those which have a relatively high dielectric constant are more preferred. As for the solvents which complex ions, the desirable solvents are those which under the reaction conditions have the capacity of complexing ions such as available cations. As stated previously, the solvent may provide a promoter component. Solvents having a dielectric constant at 25° C. or at its melting temperature, whichever is higher, of greater than 2 are preferred.

Illustrative of suitable polar solvents are, e.g., water, ketones, esters including lactones, amides including lactams, sulfones, sulfoxides, halogenated hydrocarbons, aromatic hydrocarbons, and the like. Illustrative of specific solvents encompassed by the above classes of polar solvents are, for example, aromatic hydrocarbons, e.g., benzene, toluene, xylene, naphthalene, alkylnaphthalene, etc.; carboxylic acids such as acetic acid, propionic acid, butyric acid, caproic acid, stearic acid, benzoic acid, cyclohexanecarboxylic acid, etc.; see the description of acyl compounds in European Patent Application No. 13,008; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; anhydrides such as phthalic anhydride, acetic anhydride, etc.; lactams such as N-alkyl caprolactams, such as N-methylcaprolactam; N-alkyl pyrrolidinones such as N-methyl pyrrolidinone; cyclic ureas such as N,N'-dimethylimidazolidone; polyols such as ethylene glycol, glycerine, erythritol, polyalkylene glycol containing two to about ten thousand repeating units; lactones such as gamma-butyrolactone; halogenated hydrocarbons such as chlorobenzene, chloroform, methylene chloride, 2,2-dichloropropane; amides such as dimethylformamide, dimethylacetamide, hexamethyl-phosphoramide; sulfones such as sulfolane, dimethylsulfone; the substituted sulfolanes described in U.S. application Ser. No. 61,456, filed July 27, 1979; sulfoxides such as dimethylsulfoxide, diphenyl sulfoxide; as well as many others.

Illustrative of suitable complexing solvents are the ethers, cryptands, and the like. Illustrative of specific solvents encompassed by the above classes of complexing solvents are, for example, ethers such as tetrahydrofuran, tetrahydropyran, diethyl ether, 1,2-dimethoxybenzene, 1,2-diethoxybenzene, the mono and dialkyl ethers of alkylene and polyalkylene glycols, such as ethylene glycol, of 1,2-propylene glycol, of 1,2-butylene glycol, of diethylene glycol, of di-1,2-propylene glycol, of triethylene glycol, of pentaethylene glycol (such as triglyme, tetraglyme and pentaglyme), of di-1,2-butylene glycol, of oxyethylene-oxypropylene glycols, etc., preferably those in which the alkylene group contains 2 and/or 3 carbon atoms in the divalent moiety, such as ethylene and 1,2-propylene; the cryptands such as described in U.S. Pat. No. 4,111,975, which description of cryptands, as promoters in that case, is incorporated herein by reference; the crown ethers (or Crown Ethers, as one may perfer) such as described in U.S. Pat. No. 4,162,261, which description of crown ethers, as solvents in that case, is incorporated herein by reference; as well as many others.

The choice of solvent in any particular case can be a complex decision. For example, the carboxylic acids, if employed, are also reactive with ethylene glycol, methanol and ethanol products, to produce ethylene glycol dicarboxylates, methyl carboxylates, ahd ethyl carboxylates. These carboxylates can be readily hydrolyzed to produce the alcohol products. This is not necessarily an uneconomical method to produce such products.

An important class of solvents contemplated in the practice of this invention is a mixture of the aforementioned polar solvents and the complexing solvents. Various polar solvents mixed with other polar or complexing solvents are contemplated to provide enhanced results either in terms of rates, selectivity, conversions and/or yields of one or more of the desired products. Which mixtures will achieve what result has not been determined. Combinations of, e.g., sulfolane with crown ethers, lactones, amides or ureas are contemplated as potentially useful. Combinations of, e.g., crown ethers with lactones, amides, and ureas are contemplated as potentially useful.

The iodide containing compounds employed herein may comprise most any iodide containing compound, including such compounds as iodide salts of metals such alkali metals, alkaline earth metals, cobalt diiodide, iron (II) iodide and the like. Organic iodide containing compounds may also be employed, e.g. Bis(tri-phenylphosphine)iminium iodide; tetramethylammonium iodide, triethylammonium iodide; pyridinium iodide; tetra-n-propylammonium iodide; tetra-n-butylammonium iodide; tetraphenylphosphonium iodide; tetraphenyl-arsonium iodide; tetra-n-butylphosphonium iodide; phenyltrimethylammonium iodide; and the like. The addition of such iodide salts is beneficial to provide the formation of ethylene glycol at a substantial rate. Generally, an increase in the concentration of iodide promoter increases the overall rate to ethylene glycol although the selectivity to glycol may decrease.

It is believed that the process may be carried out in the presence of a promoter although selection of the promoter is not clearly understood. A promoter, in the context of this invention, is a material provided to the reaction which provides a promotional effect in that it enhances the production (viz., rate, yield, or efficiency) of any of the products, or it improves the selectivity of the reaction toward the products.

The promoter can be any material used in miniscule quantities to a material employed in maximum quantities the effectiveness of which will in large measure be dependent upon the reaction conditions selected. Representative of the promoters employed in the instant process are iodide containing compounds. It is believed that other Lewis base promoters may also be employed, as aforementioned.

Though the process of this invention is capable of providing a combination of ethylene glycol, ethanol and methanol, in many instances one or more of them is formed as a minor component only. Because ethylene glycol is the most valued of the products, its production obviously makes this process attractive. By the same reasoning, ethanol's higher market value than methanol also enhances the commercial attractiveness of this process. A process which produces the same amount of ethylene glycol and produces more ethanol will have more commercial attractiveness, assuming all other factors are equal.

The relative amounts of carbon monoxide and hydrogen which are initially present in the reaction mixture can be varied over a wide range. In general, the molar ratio of $CO:H_2$ is in the range of from about 40:1 to about 1:40, suitably from about 20:1 to about 1:20, and preferably from about 10:1 to about 1:10. It is to be understood, however, that molar ratios outside the broadest of these ranges may be employed. Substances or reaction mixtures which give rise to the formation of carbon monoxide and hydrogen under the reaction conditions may be employed instead of the mixtures comprising carbon monoxide and hydrogen which are used in preferred embodiments in the practice of the invention. For instance, the product alcohols are contemplated as obtainable by using mixtures containing carbon dioxide and hydrogen. Mixtures of carbon dioxide, carbon monoxide and hydrogen can also be employed. If desired, the reaction mixture can comprise steam and carbon monoxide.

The quantity of catalyst employed is not narrowly critical and can vary over a wide range. In general, the process is desirably conducted in the presence of a catalytically effective quantity of the active ruthenium species which gives a suitable and reasonable reaction rate. The presence of the catalytic species is indicated by the presence of two ruthenium carbonyl complexes, i.e. $Ru(CO)_3I_3^-$ and $HRu_3(CO)_{11}^-$. It has been observed that the rate of ethylene glycol formation is related to the ratio of these complexes such that although their combined presence indicates the presence of the active ruthenium catalyst, the rate to ethylene glycol increases if the mole ratio of $Ru(CO)_3I_3^-$ to $HRu_3(CO)_{11}^-$ is between about 0.01 and about 2, preferably between about 0.2 and about 1. The reaction can proceed when employing as little as about $1 \times 10^{-6}$ weight percent, and even lesser amounts, of ruthenium based on the total weight of reaction mixture (i.e., the liquid phase mixture). The upper concentration limit can be quite high, e.g., about 30 weight percent ruthenium, and higher, and the realistic upper limit in practicing the invention appears to be dictated and controlled more by economics in view of the cost of ruthenium. Since the rate of conversion of synthesis gas may be dependent upon the concentration of ruthenium employed, higher concentrations achieving higher rates, then large concentrations may prove to be a most desirable embodiment of this invention. Depending on various factors such as the promoter (if employed), the partial pressures of carbon monoxide and hydrogen, the total operative pressure of the system, the operative temperature, the choice of solvent, and other considerations, a catalyst concentration of from about $1 \times 10^{-3}$ to about 20 weight percent ruthenium (contained in the complex catalyst) based on the total weight of reaction mixture, is generally desirable in the practice of the invention.

The temperature which may be employed in practicing the process may vary over a wide range of elevated temperatures. In general, the process can be conducted at a temperature between 50° C. and about 400° C. and higher. Temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, catalyst, solvent, or promoter instability may occur. Notwithstanding these factors, reaction will continue and the alcohols and/or their derivatives will be produced. Additionally, one should take notice of the equilibrium reaction for forming ethylene glycol:

$$2CO + 3H_2 = HOCH_2CH_2OH$$

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher operative pressures, however, do not represent preferred embodiments of the invention in view of the high investment costs associated with erecting chemical plants which utilize high pressure utilities and the necessity of fabricating equipment capable of withstanding such enormous pressures. Preferred temperatures are between about 100° C. and about 350° C., and most desirably between about 150° C. and about 300° C.

The process is suitably effected over a wide superatmospheric pressure range. At pressures in the direction of and below about 500 psia (35.15 kg/cm²) the rate of desired product formation is quite slow, and consequently, relatively faster reaction rates and/or higher conversions to the desired products can be obtained by employing higher pressures, e.g., pressures of at least about 1,000 psia (70.31 kg/cm²). Pressures as high as 20,000 to 50,000 psia (3,515,35 kg/cm²), and higher, can be employed but there is no apparent advantage in using such pressures, and any advantage that could be reasonably contemplated would be easily offset by the very unattractive plant investment outlay required for such high pressure equipment and the costs associated with such high pressure operations. Therefore, the upper pressure limitation is approximately 15,000 psia (1,054.6 kg/cm²). Effecting the process below about 15,000 (1,054.6 kg/cm²), especially below about 10,000 psia (703.1 kg/cm²), results in significant cost advantages which are associated with lower pressure equipment requirements and operating costs. A suitable pressure range is from about 500 psia (35.15 kg/cm²) to about 12,000 psia (878.84 kg/cm²). The pressure referred to above represents the total pressure of hydrogen and carbon monoxide.

The process is effected for a period of time sufficient to produce the desired alcohol products and/or derivatives thereof. In general, the residence time to produce the desired products can vary from minutes to a number of hours, e.g., from a few minutes to 24 hours, and longer. It is readily appreciated that the residence period (time) will be influenced to a significant extent by the reaction temperature, the concentration and choice of promoter and ruthenium source, the total gas pressure and the partial pressure exerted by its components, the concentration and choice of solvent, and other factors. The synthesis of the desired product(s) by the reaction of hydrogen with carbon monoxide is suitably conducted under operative conditions which give reasonable reaction rates and/or conversions.

The process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent and possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst precursor may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the process especially to maintain the desired molar ratios of and the partial pressures exerted by the reactants.

As intimated previously, the operative conditions can be adjusted to optimize the conversion of the desired product and/or the economics of the process. In a continuous process, for instance, when it is preferred to operate at relatively low conversions, it is generally desirable to recirculate unreacted synthesis gas with/without make-up carbon monoxide and hydrogen to the reactor. Recovery of the desired product can be achieved by methods well-known in the art such as by distillation, fractionation, extraction, and the like. A fraction comprising ruthenium complexes, generally contained in byproducts and/or the solvent, can be recycled to the reaction zone, if desired. All or a portion of such fraction can be removed for recovery of the ruthenium values or regeneration thereof, if necessary. Fresh ruthenium precursor, promoter and/or solvent, can be intermittently added to the recycle stream or directly to the reaction zone, if needed.

Many embodiments of the ruthenium carbonyl complexes, promoter and solvent combinations encompassed by this invention are sufficiently stable to allow repeated use of the ruthenium carbonyl complexes. This is especially noted when the promoter is an alkali metal halide, particularly and preferably an alkali metal iodide. For example, the process of this invention can be continuously operated in a pressure reactor into which is continuously fed synthesis gas. The velocity of the synthesis gas is sufficient to strip products of the reaction out of reactor leaving behind in the reactor the ruthenium carbonyl complex, promoter and solvent combination. The products are separated from the unreacted synthesis gas and the synthesis gas is recycled to the reactor. The products, in this embodiment, are recovered free of ruthenium, Lewis base, if employed, and solvent. In this embodiment, the catalyst need not be removed from the reactor to a recovery zone for separating product. Thus a catalyst treatment step is avoided. The examples below depict batch reactions; however, the above continuous gas recycle process can be operated in a similar manner. That is, the batch reactor simulates the continuous reactor except for the gas sparging and continuous gas recycle.

Although this invention has been described with respect to a number of details, it is not intended that this invention should be limited thereby. Moreover, the examples which follow are intended solely to illustrate a variety, including the most favorable, embodiments of this invention and are not intended in any way to limit the scope and the intent of this invention.

EXPERIMENTAL PROCEDURE

The following procedure was employed in the examples 1 to 26.

A 150 ml. capacity stainless steel reactor capable of withstanding pressures up to 3,000 atmospheres was charged with a mixture of solvent, catalyst precursor, and optionally a promoter, as indicated below. The reactor was sealed and charged with carbon monoxide to a pressure of 500 pounds per square inch gauge (psig), 36.19 Kg/cm$^2$. In some cases the gaseous contents of the reactor are vented to remove oxygen. In these cases the reactor is then repressurized to about 500 psig. (This venting procedure may be repeated if desired.)

Heat was then applied to the reactor and its contents, (intially at about 55° C. or as otherwise indicated); when the temperature of the mixture inside the reactor reached the designated reaction temperature, as measured by a suitable placed thermocouple, addition of carbon monoxide and hydrogen (H$_2$:CO equals the designated mole ratio) was made to bring the pressure to the specified reaction pressure. The temperature was maintained at the desired value for the reported time period. During this period of time, additional carbon monoxide and hydrogen were added whenever the pressure inside the reactor dropped by more than about 500 psig. (36.19 Kg/cm$^2$) over the entire reaction period.

After the reaction period, the reaction vessel was cooled to room temperature, the reaction vessel vented and the reaction products removed. Analysis of the reaction mixture was made by gas chromatographic methods.

The various rates set forth in the following examples are average rates for the particular product and are determined by measuring the net production of product for the reaction period and assuming a nominal reaction volume of 75 ml.

In the following examples, the following procedure was employed:

The infrared spectra of the reaction mixtures were analyzed by withdrawing a sample from a sample bottle blanketed with a nitrogen atmosphere. The sample is placed in an infrared cell having $CaF_2$ windows separated by a 0.1 mm spacer. If necessary, the sample was diluted with the solvent employed in carrying out the reaction. The infrared spectra were recording using a Perkin-Elmer 281B infrared spectrophotometer with an infrared cell containing reaction solvent being placed in the reference beam.

Figure 3:
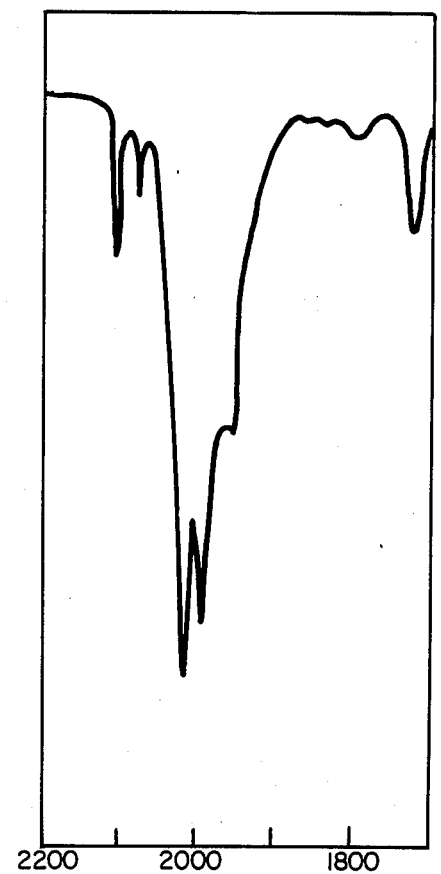
FIG. 3 depicts the infrared spectrum of a 2:1 molar mixture of PPN [$HRu_3(CO)_{11}$] and PPN [$Ru(CO)_3I_3$], respectively, prior to use in the process according to this invention.
Figure 2:
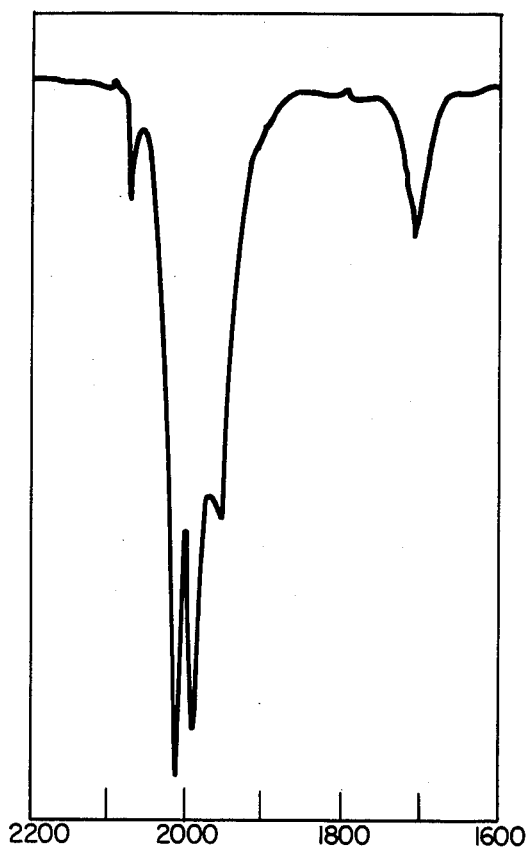
FIG. 2 depicts the infrared spectrum of PPN [$HRu_3(CO)_{11}$], hereinafter discussed, prior to use in the process.
Figure 4:
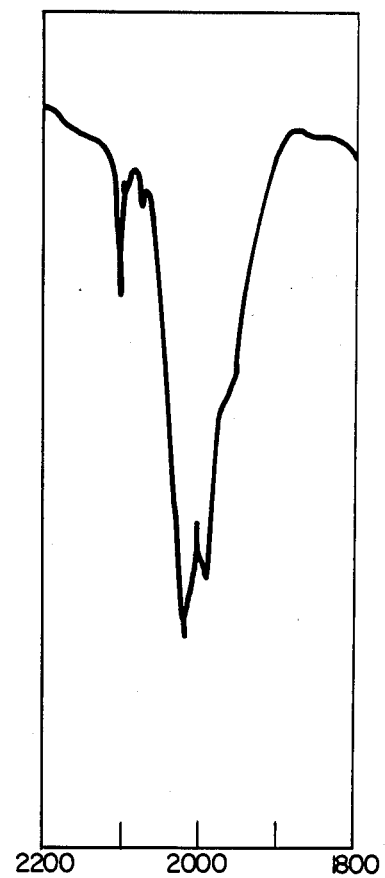
FIG. 4 depicts the infrared spectrum of a catalytic mixture according to this invention obtained from the $Ru_3(CO)_{12}$ and sodium iodide after being employed in the process (as employed in Example 1, hereinafter discussed).
Figure 5:
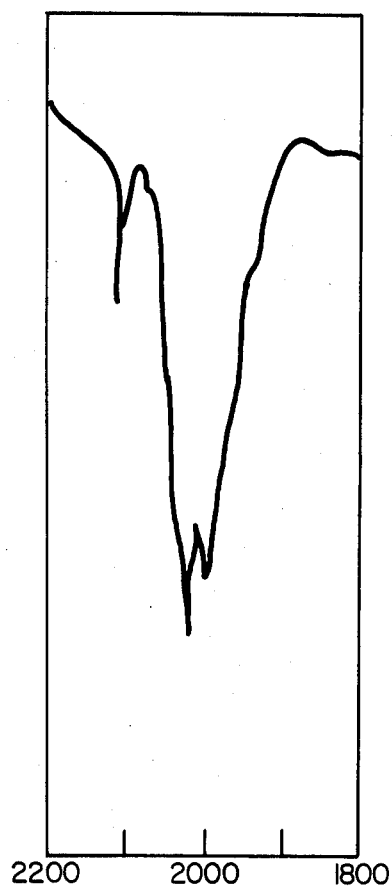
FIG. 5 depicts the infrared spectrum of a reaction mixture after the process is carried out wherein a mixture PPN [$HRu_3(CO)_{11}$] and PPN[$Ru_3(CO)_3I_3$] was employed in a 2:1 molar ratio (as employed in Example 4, hereinafter discussed).

FIGS. 1–3 show, respectively, the infrared spectra of $PPN[Ru(CO)_3I_3]$ in $CH_2Cl_2$; $PPN[HRu_3(CO)_{11}]$ in $CH_2Cl_2$; and of a mixture of $PPN[HRu_3(CO)_{11}]$ and $PPN[Ru(CO)_3I_3]$ at a 2:1 molar ratio, in sulfolane. FIG. 4 and FIG. 5 show, respectively, the infrared spectra of reaction mixtures (after catalysis) from Examples 1 and 4.

EXAMPLES 1–12

The following examples were carried out to demonstrate the ruthenium carbonyl catalyst employed in the process of the invention as indicated by the presence of a synergistic mixture of $Ru(CO)_3I_3^-$ and $HRu(CO)_{11}^-$. In each example, as set forth in Table I, the indicated ruthenium carbonyl complex was employed according to the above described experimental procedure. The process conditions, number of millimoles of ruthenium carbonyl employed, rate of formation of ethylene glycol, rate of formation of methanol and milligram atoms of ruthenium are set forth in Table I.

EXAMPLES 13–25

The following examples were carried out to determine the ratio of $Ru(CO)_3I_3^-$ to $HRu_3(CO)_{11}^-$ to be employed in the process. Examples 14 to 19, inclusive, were carried out by employing 1.72 millimoles of $PPN[HRu_3(CO)_{11}]$ while varying the amount of $PPN[Ru(CO)_3I_3]$ as shown for examples 14 to 19 in Table II. Examples 20 to 25, inclusive, were carried by employing 0.86 millimoles of $PPN[Ru(CO)_3I_3^-]$ while varying the amount of $PPN[HRu_3(CO)_{11})]$ as shown in Table II.

Figure 7:
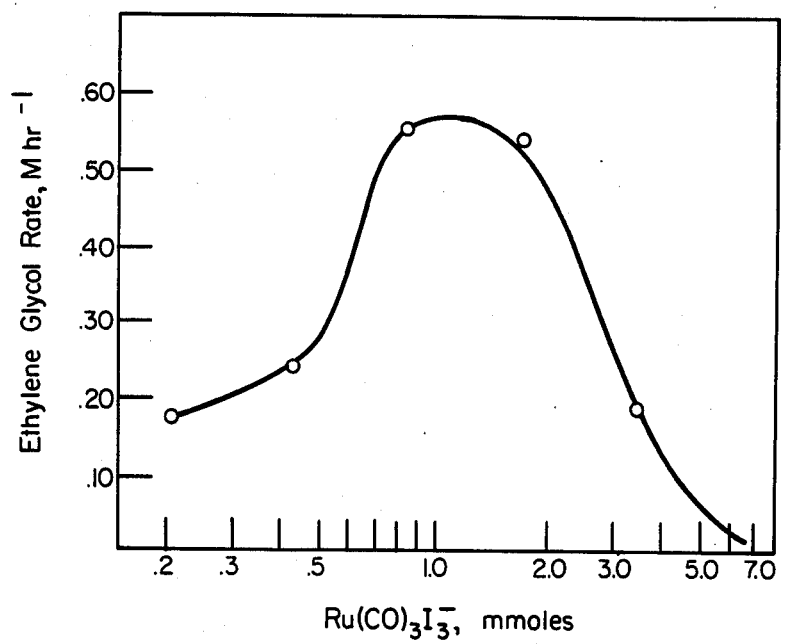
FIG. 7 and FIG. 8 depict the relationship between tne ratio of moles of $Ru(CO)_3I_3^-$ to moles of $HRu_3(CO)_{11}^-$ and the rate of formation of ethylene glycol. (Table II.)
Figure 8:
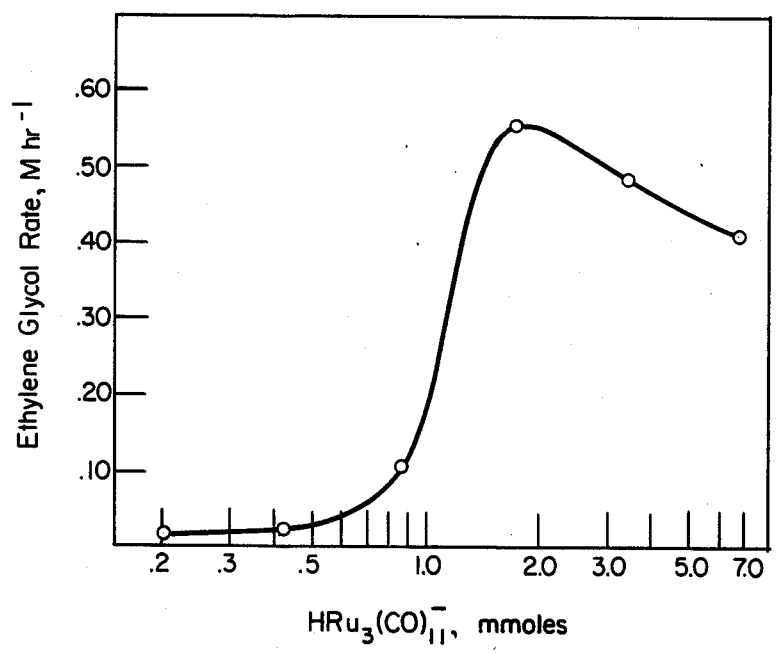

The results of examples 13 to 25 are graphically displayed in FIGS. 7 and 8.

TABLE I[a]

| Example | Complex | mmoles | Ru, mg-atom | EG Rate | MeOH Rate |
|---|---|---|---|---|---|
| 1 | $Ru_3(CO)_{12}$ | 2.0 | 6.0 | .38 | 2.28 |
| 2 | $PPN[HRu_3(CO)_{11}]$ | 2.0 | 6.0 | .10 | 1.64 |
| 3 | $PPN[HRu_3(CO)_3I_3]$ | 6.0 | 6.0 | 0 | 0 |
| 4 | $PPN[HRu_3(CO)_{11}]$ $PPN[Ru(CO)_3I_3]$ | 1.72 0.86 | 6.0 | .41 | 2.92 |
| 5 | $PPN[HRu_3(CO)_{11}$ $PPN[Ru(CO)_3I_3]$ | 1.72 1.72 | 6.9 | .47 | 2.90 |
| 6 | $PPN[HRu_3(CO)_{11}]$ $PPN[Ru(CO)_3I_3]$ | 3.44 0.86 | 11.2 | .48 | 2.92 |
| 7 | $PPN[HRu_3(CO)_{11}]$ $PPN[Ru(CO)_3I_3]$ | 1.72 0.86 | 6.0 | .17[b] | 1.10[b] |
| 8 | $(PPN)_2[Ru_6C(CO)_{16}]$ | 1.0 | 6.0 | .11 | 1.19 |
| 9 | $(PPN)_2[Ru_6C(CO)_{16}]$ $PPN[Ru(CO)_3I_3]$ | 0.86 0.86 | 6.0 | 0 | 0.16 |
| 10 | $(PPN)_2[Ru_6C(CO)_{16}]$ $Ru_3(CO)_{12}$ | 1.0 2.0 | 12.0 | .45 | 2.55 |
| 11 | $Ru_3(CO)_{12}$ | 1.0 | 3.0 | .35 | 1.58 |
| 12 | $Ru_3(CO)_{12}$ | 1.0 | 3.0 | .35[c] | 1.91[c] |

[a]Conditions: 75 mL sulfolane solvent, 12500 psi 1:1 $H_2$/CO, 230° C., 18 mmoles NaI. Rates are M hr$^{-1}$. (PPN = bis[bis[triphenylphosphine] iminium).
[b]No NaI promoter.
[c]PPNI (18 mmoles) instead of NaI.

TABLE II[a]

| Example | $PPN[Ru(CO)_3I_3]$ (mmoles) | $PPN[HRu_3(CO)_{11}]$ (mmoles) | Total Ru mg-atoms | EG Rate M hr$^{-1}$ | MeOH Rate M hr$^{-1}$ |
|---|---|---|---|---|---|
| 13 | — | — | 6.00[b] | .55 | 4.62 |
| 14 | .21 | 1.72 | 5.37 | .18 | 2.60 |
| 15 | .42 | 1.72 | 5.59 | .24 | 2.95 |
| 16 | .86 | 1.72 | 6.00 | .53 | 4.67 |
| 17 | 1.72 | 1.72 | 6.88 | .54 | 5.55 |
| 18 | 3.44 | 1.72 | 8.60 | .19 | 2.84 |
| 19 | 6.88 | 1.72 | 12.04 | .02 | 0.08 |
| 20 | .86 | .21 | 1.49 | .01 | 0.10 |
| 21 | .86 | .43 | 2.15 | .02 | 0.11 |
| 22 | .86 | .86 | 3.44 | .11 | 1.66 |
| 23 | .86 | 1.72 | 6.00 | .53 | 4.67 |
| 24 | .86 | 3.44 | 11.18 | .48 | 4.21 |
| 25 | .86 | 6.88 | 21.50 | .41 | 5.43 |

[a]Conditions: 75 mL sulfolane solvent, 12500 psi 1:1 $H_2$/CO, 230°, 36 mmoles NaI. (PPN = bis[triphenylphosphine]iminium).
[b]Charged as $Ru_3(CO)_{12}$; standard run.

EXAMPLE 26

Figure 6:
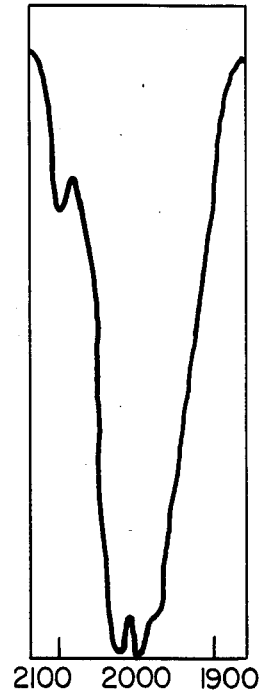
FIG. 6 depicts the infrared spectrum of the reaction mixture of Example 26, at a pressure of 8000 psig.

A catalytic reaction was begun as described above, employing 1 mmole of $Ru_3(CO)_{12}$, 18 mmoles of KI, and 75 ml of sulfolane solvent under a total pressure of 8000 psi of synthesis gas (1:1 $H_2$:CO), at 230° C. The infrared spectrum of the catalytic solution was recorded during catalysis by use of the high-pressure infrared cell and spectrophotometer described elsewhere (J. L. Vidal and W. E. Walker, Inorg. Chem., 19, pages 896–903 (1980)). The infrared spectra of the catalytic solution is depicted in FIG. 6.

In examples 27 to 30 recorded in Table III below, the following procedure was employed:

A 500 ml stainless steel bomb reactor containing a removable glass liner was charged with a mixture of $Ru_3(CO)_{12}$, solvent and Lewis base as designated below. Carbon monoxide and hydrogen were then added in the designated ratios to the reactor to attain a pressure therein of 3,000 psig (211.95 kg/cm$^2$) at 25° C. The reactor was rocked and the contents heated to the reaction temperature and maintained at this temperature for two hours while rocking the reactor. The pressure was maintained at the specified reaction pressure during the indicated period of the reaction. The reactor was then cooled and vented. The contents of the reactor were removed and analyzed by gas chromatography. Table III directly follows.

The following procedure was employed in the examples recorded in Table IV below:

A 150 ml capacity stainless steel reactor capable of withstanding pressures up to 3,000 atmospheres was charged with a mixture of solvent, ruthenium as triruthenium dodecacarbonyl and Lewis base promoter, as indicated below. The reactor was sealed and charged with a gaseous mixture, containing carbon monoxide and hydrogen in the ratios specified below, to a pressure of 2,500 pounds per square inch gauge (psig) (176.8 kg/cm$^2$). Heat was applied to the reactor and its contents; when the temperature of the mixture inside the reactor reached the designated reaction temperature recited below, as measured by a suitably placed thermocouple, addition of carbon monoxide and hydrogen ($H_2$:CO = designated mole ratio) was made to bring the pressure to the specified reaction pressure recited below. The temperature (in °C.) was maintained at the desired value for the reported time. During this period of time additional carbon monoxide and hydrogen was added whenever the pressure inside the reactor dropped by more than 500 psig (36.19 kg/cm$^2$). With these added repressurizations the pressure inside the reactor was maintained at the reaction pressure ±500 psig (36.19 kg/cm$^2$) over the entire reaction period.

After the reaction period, the vessel and its contents were cooled to room temperature, the excess gas vented and the reaction product mixture was removed. Analysis of the reaction product mixture was made by gas chromatographic analysis. Table IV directly follows.

TABLE III

| Example Nos. | Millimoles of Ruthenium | Lewis base | Millimoles of Lewis base | Solvent | Milliliters of Solvent | Reaction Temperature °C. | Reaction Pressure psig[3] | $H_2$/CO Ratio | Reaction Period hours | Grams of Ethylene Glycol Recovered | Grams of Methanol Recovered | Grams of Ethanol Recovered |
|---|---|---|---|---|---|---|---|---|---|---|---|---|
| 27 | 2.34 | LiI | 14.9 | Sulf[1] | 40 | 230 | 5,000 | 1:1 | 2 | .10 | 4.25 | .25 |
| 28 | 2.34 | KI | 15.0 | Sulf | 40 | 230 | 5,000 | 1:1 | 2 | .16 | 5.76 | .31 |
| 29 | 2.34 | NaI | 15.0 | Sulf | 40 | 230 | 5,000 | 1:1 | 2 | .17 | 6.49 | .36 |
| 30 | 2.34 | NaI | 15.0 | NMP[2] | 50 | 230 | 5,000 | 1:1 | 2 | .16 | 4.12 | .09 |

[1]"Sulf" is an abbreviation for sulfolane.
[2]"NMP" is an abbreviation for N—methylpyrrolidinone.
[3]5,000 psig = 352.57 kg/cm$^2$.

TABLE IV

| Example Nos. | Millimoles of Ruthenium | Lewis base | Millimoles of Lewis base | Solvent | Milliliters of Solvent | Reaction Temperature °C. | Reaction Pressure, psig (kg/cm$^2$) | $H_2$/CO Ratio | Reaction Period, hours | Grams of Ethylene Glycol Recovered | Grams of Methanol Recovered | Grams of Ethanol Recovered[11] |
|---|---|---|---|---|---|---|---|---|---|---|---|---|
| 31 | — | LiI | 22.4 | Sulf[1] | 75 | 230 | (352.6) 5,000 | 1:1 | 4 | — | — | — |
| 32 | 3.51 | LiI | 22.4 | Sulf[1] | 75 | 230 | (352.6) 5,000 | 1:1 | 4 | 1.33 | 3.69 | — |
| 33 | 3.51 | LiI | 22.4 | Sulf[1] | 75 | 230 | (879.9) 12,500 | 1:1 | 1.15 | 1.42 | 5.36 | 0.14 |
| 34 | 3.51 | LiI | 22.4 | Sulf[1] | 75 | 230 | (879.9) 12,500 | 1:1 | 1.20 | 1.17 | 5.44 | 1.06 |
| 35 | — | NaI | 18 | 18-C-6[2] | 75 | 230 | (879.9) 12,500 | 1:1 | 4 | — | — | — |
| 36 | 3 | NaI | 6 | 18-C-6[2] | 75 | 230 | (879.9) 12,500 | 1:1 | 1.75 | 1.68 | 6.26 | 1.0 |
| 37 | 3 | NaI | 18 | 18-C-6[2] | 75 | 230 | (879.9) 12,500 | 1:1 | .83 | 1.38 | 7.91 | 1.06 |
| 38 | 3 | NaI | 36 | 18-C-6[2] | 75 | 230 | (879.9) 12,500 | 1:1 | .47 | 1.23 | 7.63 | 0.81 |
| 39 | 3 | NaI | 18 | 18-C-6[2] | 75 | 260 | (879.9) 12,500 | 1:1 | .33 | 1.20 | 8.30 | 1.88 |
| 40 | 3 | KI | 3 | 18-C-6[2] | 75 | 230 | (879.9) 12,500 | 1:1 | 2.30 | 1.51 | 5.75 | 0.70 |
| 41 | 3 | KI | 6 | 18-C-6[2] | 75 | 230 | (879.9) 12,500 | 1:1 | 1.50 | 1.38 | 6.53 | 0.71 |
| 42 | 3 | KI | 12 | 18-C-6[2] | 75 | 230 | (879.9) 12,500 | 1:1 | .83 | 1.22 | 6.73 | 0.63 |
| 43 | 9 | KI | 12 | TG[3] | 75 | 230 | (879.9) 12,500 | 1:1 | 2.83 | .86 | 6.27 | 0.81 |
| 44 | 3 | NaI | 6 | TG[3] | 75 | 230 | (879.9) 12,500 | 1:1 | 4 | .48 | 6.28 | 1.08 |
| 45 | 3 | LiI | 24 | TG[3] | 75 | 260 | (879.9) 12,500 | 1:1 | 1.30 | .31 | 3.42 | 3.40 |
| 46 | 9 | KOAc[9] | 48 | TG[3] | 75 | 260 | (879.9) 12,500 | 1:1 | 2.10 | .08 | 7.13 | — |
| 47 | 3 | K$_3$PO$_4$ | 18 | 18-C-6[2] | 75 | 230 | (879.9) 12,500 | 1:1 | 3.95 | 1.54 | 5.17 | 1.10 |

TABLE IV-continued

| Example Nos. | Millimoles of Ruthenium | Lewis base | Millimoles of Lewis base | Solvent | Milliliters of Solvent | Reaction Temperature °C. | Reaction Pressure, psig (kg/cm$^2$) | H$_2$/CO Ratio | Reaction Period, hours | Grams of Ethylene Glycol Recovered | Grams of Methanol Recovered | Grams of Ethanol Recovered[11] |
|---|---|---|---|---|---|---|---|---|---|---|---|---|
| 48 | 3 | PPNI[8] | 3 | TG[3] | 75 | 230 | 12,500 (879.9) | 1:1 | 2.33 | .63 | 6.63 | 0.67 |
| 49 | 3 | KI | 3 | H$_2$O | 75 | 230 | 12,500 (879.9) | 1:1 | 4 | .90 | — | 1.32 |
| 50 | 3 | KI | 18 | H$_2$O | 75 | 230 | 12,500 (879.9) | 1:1 | 4 | 1.22 | — | 2.27 |
| 51 | 9 | KI | 30 | THF[4] | 75 | 230 | 12,500 (879.9) | 1:1 | 4 | .017 | .215 | — |
| 52 | 3.51 | LiI | 15.9 | BL[5] | 75 | 230 | 12,500 (879.9) | 1:1 | 0.9 | .84 | 2.65 | 2.60 |
| 53 | 3 | KI | 18 | 18-C-6[2] | 75 | 230 | 12,500 (879.9) | 1:1 | .75 | 1.29 | 6.58 | 0.12 |
| 54 | 9 | KI | 54 | 18-C-6[2] | 75 | 230 | 12,500 (879.9) | 1:1 | .22 | 2.07 | 7.88 | 1.22 |
| 55 | 15 | KI | 60 | 18-C-6[2] | 75 | 230 | 12,500 (879.9) | 1:1 | .20 | 2.40 | 7.04 | 1.39 |
| 56 | 3 | KI | 18 | NMP[6] | 75 | 230 | 12,500 (879.9) | 1:1 | .65 | .20 | 7.15 | 0.15 |
| 57 | 3 | NaI | 18 | Sulf[1] | 75 | 230 | 12,500 (879.9) | 1:1 | 1.25 | 1.55 | 4.75 | 0.13 |
| 58 | 9 | NaI | 54 | Sulf[1] | 75 | 200 | 12,500 (879.9) | 1:1 | 1.42 | 2.89 | 4.36 | 0.16 |
| 59 | 3 | KOAc[9] | 18 | Sulf[1] | 75 | 230 | 12,500 (879.9) | 1:1 | 4 | .40 | 4.30 | — |
| 60 | 9 | KI | 54 | NMP[6] | 75 | 180 | 12,500 (879.9) | 1:1 | 1.83 | .41 | 2.68 | — |
| 61 | 3 | CsI | 18 | 18-C-6[2] | 75 | 230 | 12,500 (879.9) | 1:1 | .70 | 1.15 | 7.83 | 0.88 |
| 62 | 3 | KI | 18 | NMP[6] | 75 | 210 | 15,000 (1,054.6) | 1:1 | .83 | .27 | 5.69 | — |
| 63 | 3 | KI | 18 | NMP[6] | 75 | 180 | 20,000 (1,467.2) | 1:1 | 2.17 | .33 | 2.84 | — |
| 64 | 3 | KI | 18 | NMP[6] | 75 | 230 | 12,500 (879.9) | 1:1 | .60 | .11 | 7.42 | — |
| 65 | 3 | KI | 18 | 18-C-6[2] | 75 | 230 | 12,500 (879.9) | 1:1 | .82 | 1.13 | 9.38 | 1.07 |
| 66 | 3 | PPNI[8] | 18 | NMP[6] | 75 | 230 | 12,500 (879.9) | 1:1 | .5 | .23 | 6.91 | .31 |
| 67 | 3 | CsI | 18 | NMP[6] | 75 | 230 | 12,500 (879.9) | 1:1 | .63 | .19 | 7.2 | .53 |
| 68 | 3 | NaI | 18 | Sulf[1] | 75 | 230 | 12,500 (879.9) | 1:1 | 1.03 | .79 | 3.16 | .17 |
| 69 | 9 | NaI | 54 | Sulf[1] | 75 | 200 | 12,500 (879.9) | 1:1 | 1.17 | 2.06 | 3.79 | .16 |
| 70 | 9 | KI | 54 | 18-C-6[2] | 75 | 210 | 12,500 (879.9) | 1:1 | .7 | 1.99 | 7.65 | .48 |
| 71 | 15 | KI | 90 | Sulf[1] | 70 | 180 | 12,500 (879.9) | 1:1 | 2 | 2.46 | 2.03 | — |
| 72 | 3 | KI | 90 | Sulf[1] | 70 | 180 | 12,500 (879.9) | 1:1 | 2 | .31 | .64 | — |
| 73 | 5 | KI | 30 | Sulf[1] | 75 | 180 | 12,500 (879.9) | 1:1 | 2 | .66 | .80 | — |
| 74 | 30 | KI | 180 | Sulf[1] | 65 | 180 | 12,500 (879.9) | 1:1 | 1.68 | 4.19 | 2.14 | — |
| 75 | 9 | KI | 59 | 18-C-6[2] | 75 | 180 | 12,500 (879.9) | 2:1 | 1.95 | 2.41 | 4.91 | — |
| 76 | 3 | KI | 18 | Sulf[1] | 75 | 210 | 12,500 (879.9) | 2:1 | 2 | 1.34 | 4.10 | — |
| 77 | 3 | KI | 18 | 18-C-6[2] | 75 | 210 | 12,500 (879.9) | 2:1 | 1.82 | 1.16 | 8.21 | — |
| 78 | 3 | KI | 18 | Sulf[1] | 75 | 210 | 12,500 (879.9) | 1:1 | 2 | 1.39 | 3.40 | — |
| 79 | 3 | KI | 60 | Sulf[1] | 75 | 210 | 12,500 (879.9) | 1:1 | 1.25 | 1.36 | 4.32 | — |
| 80 | 9 | KI | 60 | Sulf[1] | 75 | 180 | 12,500 (879.9) | 1:1 | 2 | 2.39 | 2.49 | — |
| 81 | 9 | KI | 60 | Sulf[1] | 75 | 180 | 12,500 (879.9) | 2:1 | 2 | 2.40 | 3.50 | — |
| 82 | 3 | CsCl | 18 | 18-C-6[2] | 75 | 230 | 12,500 (879.9) | 1:1 | 4 | .30 | 5.61 | — |
| 83 | 9 | KI | 54 | 18-C-6[2] | 75 | 200 | 12,500 (879.9) | 1:1 | .65 | 1.66 | 6.05 | — |
| 84 | 15 | KI | 60 | 18-C-6[2] | 75 | 230 | 12,500 (879.9) | 1:1 | .17 | 1.79 | 6.60 | — |
| 85 | 15 | KI | 60 | 18-C-6[2] | 75 | 260 | 12,500 (879.9) | 1:1 | .13 | .65 | 5.37 | 2.90 |

TABLE IV-continued

| Example Nos. | Millimoles of Ruthenium | Lewis base | Millimoles of Lewis base | Solvent | Milliliters of Solvent | Reaction Temperature °C. | Reaction Pressure, psig (kg/cm²) | H₂/CO Ratio | Reaction Period, hours | Grams of Ethylene Glycol Recovered | Grams of Methanol Recovered | Grams of Ethanol Recovered[11] |
|---|---|---|---|---|---|---|---|---|---|---|---|---|
| 86 | 15 | KI | 60 | 18-C-6[2] | 75 | 200 | (879.9) 12,500 | 1:1 | .47 | 2.96 | 6.86 | — |
| 87 | 30 | KI | 180 | Sulf[1] | 65 | 230 | (879.9) 12,500 | 1:1 | .17 | 2.31 | 5.55 | — |
| 88 | 6 | LiI | 12 | Sulf[1] | 75 | 230 | (564.2) 8,000 | 1:1 | 2.03 | 1.11 | 4.55 | 0.74 |
| 89 | 3 | KI | 18 | Sulf[1] | 75 | 230 | (879.9) 12,500 | 1:1 | 1.08 | 1.15 | 4.91 | — |
| 90 | 45 | KI | 180 | Sulf[1] | 65 | 230 | (879.9) 12,500 | 1:1 | 0.12[7] | 2.44 | 5.2 | .32 |
| 91 | 3 | CsI | 18 | 18-C-6[2] | 75 | 230 | (879.9) 12,500 | 1:1 | 0.55 | 0.71 | 5.63 | 0.27 |
| 92 | 3 | BaI₂ | 18 | 18-C-6[2] | 75 | 230 | (879.9) 12,500 | 1:1 | 2.0 | 0.01 | 1.77 | 0.34 |
| 93 | 9 | KI | 54 | 18-C-6[2] | 75 | 260 | (564.2) 8,000 | 1:1 | 0.68 | 0.22 | 3.20 | 1.91 |
| 94 | 9 | KI | 54 | 18-C-6[2] | 75 | 280 | (564.2) 8,000 | 1:1 | 0.42 | 0.06 | 2.60 | 1.70 |
| 95 | 3 | NaI | 18 | TG[3] | 75 | 280 | (564.2) 8,000 | 1:1 | 1.72 | 0.13 | 4.67 | 1.92 |
| 96 | 9 | KOAc[9] | 48 | TG[3] | 75 | 260 | (879.9) 12,500 | 1:1 | 2.10 | 0.08 | 7.13 | 1.35 |
| 97 | 3 | CsF | 18 | 18-C-6[2] | 75 | 230 | (879.9) 12,500 | 1:1 | 4 | 0.24 | 5.95 | 0.40 |
| 98 | 3 | K₂CO₃ | 9 | NMP[6] | 75 | 230 | (879.9) 12,500 | 1:1 | 3.45 | 0.35 | 7.24 | 1.45 |
| 99 | 6 | LiI[10] | 12 | Sulf[1] | 75 | 230 | (564.2) 8,000 | 1:1 | 3.08 | 0.72 | 2.98 | 0.83 |
| 100 | 30 | KI | 180 | Sulf[1] | 75 | 200 | (438.4) 6,000 | 1:1 | 2.0 | 2.41 | 5.5 | 0.1[12] |

[1] Sulfolane
[2] 18-Crown-6 [(CH₂CH₂O)₆]
[3] Tetraglyme [CH₃O(CH₂CH₂O)₄CH₃]
[4] Tetrahydrofuran
[5] Gamma-butyrolactone
[6] N—methylpyrrolidinone
[7] Rate to ethylene glycol of 5.3 gram moles/liter hr⁻¹
[8] Bis(triphenylphosphine)iminium iodide
[9] Potassium acetate
[10] In this example, dicobalt octacarbonyl, Co₂(CO)₈ (1 millimole), was added to the reaction mixture as a source of tetracarbonyl cobaltate anion.
[11] A dash mark (—) in this column means that ethanol was not determined quantitatively, although its presence was invariably detected by vapor phase chromatographic analysis
[12] Approximately.

What is claimed is:

1. The process for making the products methanol, ethylene glycol and ethanol directly from the reaction of hydrogen and carbon monoxide which comprises reacting in a solvent-containing liquid phase a mixture of hydrogen and carbon monoxide in the presence of a ruthenium carbonyl complex catalyst at a temperature between about 50° C. and 400° C. and a pressure between about 500 psia (35.15 Kg/cm²) and 15,000 psia (1,054.6 Kg/cm²) wherein the ruthenium carbonyl catalyst is characterized by a synergistic combination of Ru(CO)₃I₃⁻ and HRu₃(CO)₁₁⁻ such being characterized by an infrared spectrum having three significant infrared bands between about plus or minus 10 cm⁻¹ of about 2100 cm⁻¹, 2015 cm⁻¹, and 1990 cm⁻¹.

2. The process of claim 1 wherein a promoter of the reaction is provided in the liquid phase.

3. The process of claim 2 wherein the solvent is polar.

4. The process of claim 2 wherein the solvent complexes ions.

5. The process of claim 1 wherein the solvent is a carboxylic acid and the products formed are corresponding derivative carboxylates.

6. The process of claim 1 wherein the temperature is between about 100° C. and about 350° C.

7. The process of claim 1 wherein the pressure is between about 500 psia (35.15 kg/cm²) and 12,500 psia (878.84 kg/cm²).

8. The process of claim 1 wherein the pressure is the total pressure of hydrogen and carbon monoxide supplied to said process.

9. The process of claim 3 wherein the solvent is a sulfone.

10. The process of claim 3 wherein the solvent is a lactam.

11. The process of claim 3 wherein the solvent is an ether.

12. The process of claim 11 wherein the solvent is a crown ether.

13. The process of claim 11 wherein the solvent is an alkyl ether of an alkylene glycol.

14. The process of claim 11 wherein the solvent is a dialkyl ether of a polyalkylene glycol.

15. The process of claim 14 wherein the solvent is tetraglyme.

16. The process of claim 3 wherein the solvent is a lactone.

17. The process of claim 16 wherein the solvent is butyrolactone.

18. The process of claim 2 wherein an iodide promoter compound is provided in the liquid phase.

19. The process of claim 18 wherein the promoter is an alkali metal iodide.

20. The process of claim 19 wherein the alkali metal iodide is sodium iodide.

21. The process of claim 19 wherein the alkali metal iodide is lithium iodide.

22. The process of claim 19 wherein the alkali metal iodide is potassium iodide.

23. The process of claim 19 wherein the. alkali metal iodide is cesium iodide.

24. The process of claim 1 wherein the carbon monoxide and hydrogen are continuously supplied to the liquid phase and product is removed continuously from said liquid phase in combination with unreacted carbon monoxide and hydrogen.

25. The process of claim 24 wherein unreacted carbon monoxide and hydrogen are recycled to the liquid phase.

26. The process of claim 25 wherein a promoter of the reaction is provided in the liquid phase.

27. The process of claim 2 wherein the amount of promoter provided to the reaction is that amount which achieves a measurable promotional effect.

28. The process of claim 18 wherein the amount of iodide promoter provided in the liquid phase ranges from about 0.1 mole to about $10^6$ moles for each gram atom of ruthenium present.

29. The process of claim 1 wherein the molar ratio of $Ru(CO)_3I_3^-$ to $HRu_3(CO)_{11}^-$ is between about 0.01 and about 2.

30. The process of claim 29 wherein the molar ratio is between about 0.2 and about 1.

31. The process of claim 1 wherein the average oxidation state of ruthenium is between about $-0.2$ and $0.25$.

* * * * *